United States Patent
Kawasaki et al.

(10) Patent No.: US 7,718,806 B2
(45) Date of Patent: May 18, 2010

(54) PROCESS FOR PRODUCTION OF CARBOSTYRIL COMPOUND

(75) Inventors: Kengo Kawasaki, Tokushima (JP); Takayuki Ikeda, Tokushima (JP); Takeshi Sekine, Tokushima (JP); Norio Fukuda, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 776 days.

(21) Appl. No.: 11/596,004

(22) PCT Filed: Apr. 7, 2006

(86) PCT No.: PCT/JP2006/307461

§ 371 (c)(1),
(2), (4) Date: Nov. 9, 2006

(87) PCT Pub. No.: WO2006/117977

PCT Pub. Date: Nov. 9, 2006

(65) Prior Publication Data

US 2007/0299262 A1    Dec. 27, 2007

(30) Foreign Application Priority Data

Apr. 28, 2005  (JP) .............. 2005-132486
Mar. 28, 2006  (JP) .............. 2006-087654

(51) Int. Cl.
    *C07D 215/38*    (2006.01)
(52) U.S. Cl. ................. 546/159; 546/153
(58) Field of Classification Search ........... 546/153, 546/159
    See application file for complete search history.

(56) References Cited

U.S. PATENT DOCUMENTS

| 4,578,381 A * | 3/1986 | Uchida et al. ........... 514/235.2 |
| 5,034,539 A | 7/1991 | Arrang et al. |
| 6,680,386 B2 | 1/2004 | Byoung-suk et al. |

FOREIGN PATENT DOCUMENTS

| JP | 60-019767 | 1/1986 |
| JP | 3-145468 | 6/1991 |
| JP | 2004-131506 A | 4/2004 |
| KR | 2003-50412 | 6/2003 |

OTHER PUBLICATIONS

Uchida, Chem pharm bull, 33(9), pp. 3775-3786, 1985.*
Ye, CA 114:121998, abstract only of Beijing Daxue xzuebao, Ziran Kexueban, 26(2), pp. 207-213, 1990.*
Y. Ye et al., "Synthesis and Physiological Activity of 1,2-dihydro-2-oxoquinoline derivatives," Beijing Daxue Xuebao, Ziran Kexueban, vol. 26, No. 2, pp. 207-213 (1990).
M. Uchida et al., "Studies on 2(1H)-quinolinone Derivatives as Gastric Antiulcer Active Agents, 2-(4-Chlorobenzoylamino)-3-[2(1H)-quinolinon-4-yl]propionic Acid and Related Compounds," Chemical & Pharmaceutical Bulletin, vol. 33, No. 9, pp. 3775 to 3786 (1985).
Minoru Uchida et al., "Development of Anti-ulcer Drug, Rebamipide," Journal of Synthetic Organic Chemistry, Japan, vol. 53, No. 12, (1995), pp. 1077-1089.
R. J. Chudgar et al., "Studies in the Synthesis of Quinoline Derivatives: Part I: Synthesis of Bromoquinolines," Journal Indian Chemical Society, vol. 46, No. 6, 1969, pp. 537-540.

* cited by examiner

Primary Examiner—D. Margaret Seaman
(74) Attorney, Agent, or Firm—Finnegan, Henderson, Farabow, Garrett & Dunner, L.L.P.

(57) ABSTRACT

The invention provides an improved process for preparing a carbostyril compound (1) or a salt thereof that is useful as a medicament, which makes it possible to prepare it more safely and efficiently.

In more detail, the invention provides an improved process for preparing the carbostyril compound (1) by heating the compound (4) with a high boiling solvent in hydrochloric acid under reflux to give the compound (5) safely; and then acylating the compound (5).

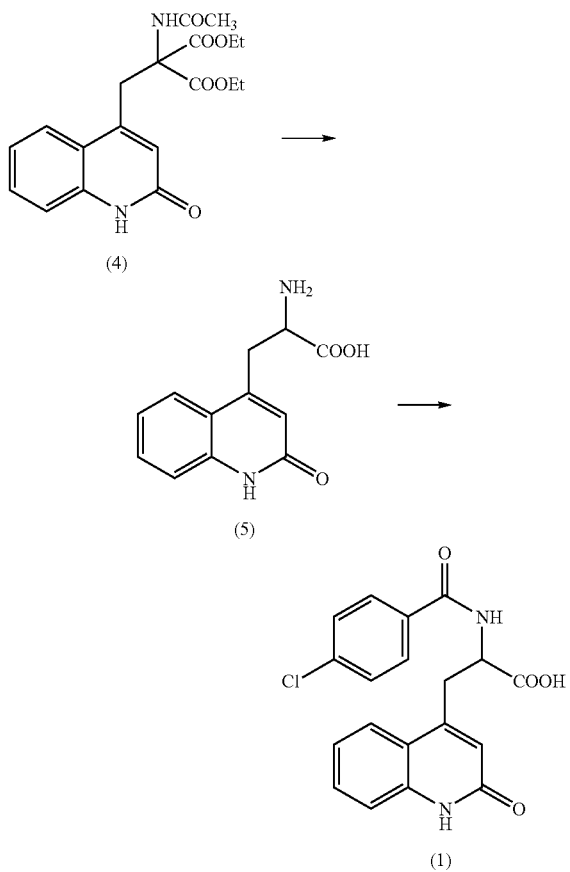

5 Claims, No Drawings

PROCESS FOR PRODUCTION OF CARBOSTYRIL COMPOUND

TECHNICAL FIELD

The invention relates to an improved process for preparing the following carbostyril compound that is useful as a medicament for treating gastric ulcer and the like, which makes it possible to prepare it more safely and efficiently.

BACKGROUND ART

The carbostyril compound of the invention, which means a carbostyril compound (chemical name: 2-(4-chlorobenzoylamino)-3-[2(1H)-quinolinon-4-yl]propionic acid) of the following formula (1), is a medicament that has a potent effect on the treatment of gastric ulcer, acute gastritis, or gastric mucosa lesion affected in acute exacerbation of chronic gastritis.

As an example of the process for preparing the carbostyril compounds (1) of the invention, a process shown in the following Scheme 1 is known (JP-A-60-19767). The process is illustrated as follows:

That is, the compound (2) is reacted with the compound (3) in the presence of a base such as sodium ethoxide to give the compound (4);

the compound (4) is hydrolyzed and decarboxylated in the presence of a mineral acid such as hydrochloric acid to prepare the compound (5); and then the compound (5) is acylated with 4-chlorobenzoyl-chloride (6) to prepare the desired compound of the formula (1).

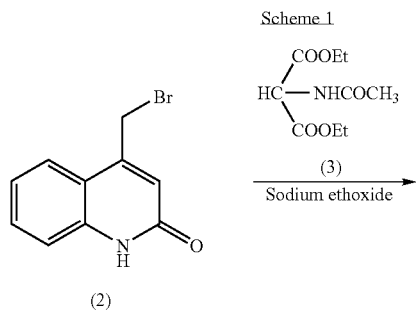

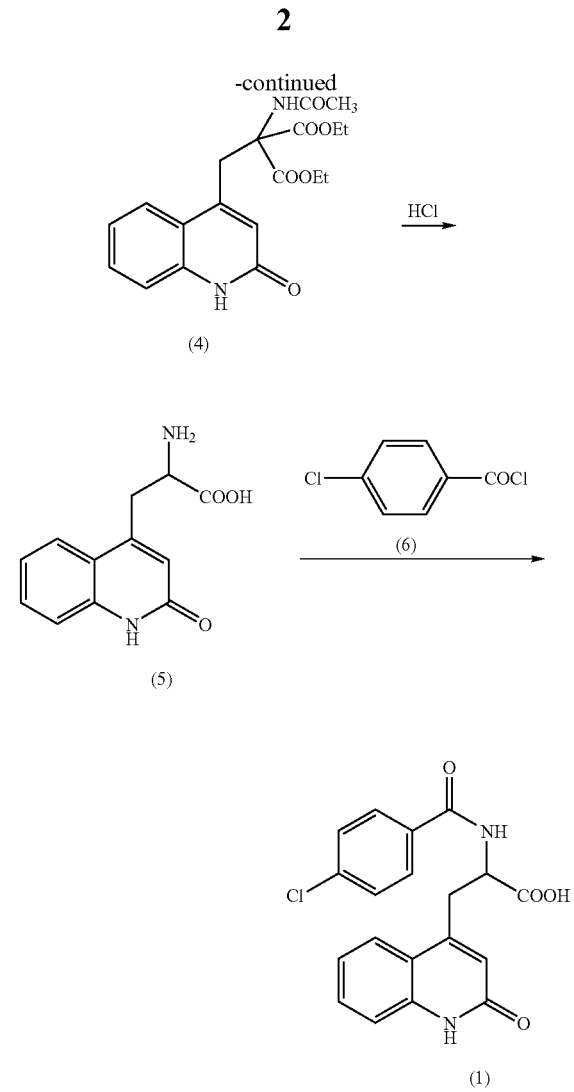

In the process for preparing the compound (5) from the compound (4) which is shown in the above scheme, the compound (4) needs to be heated under reflux, for example, in 20% hydrochloric acid. In this reaction process, however, ethanol, carbon dioxide, acetic acid and ethyl acetate are by-produced as the reaction proceeds. Accordingly, the surface of the reaction mixture is intensely bubbled by the generated carbon dioxide and additionally the bubbles do not disappear shortly. Especially when the amount of hydrochloric acid for the compound (4) is small, the surface of the reaction mixture is intensely developed by such bubbles, and hence it often becomes difficult to continue refluxing. In addition, such intense development of the surface is accompanied with a dangerous bumping, and hence the safety for the development is a big problem when the desired carbostyril compound (1) is produced in bulk. In order to prevent such bubbles, it is necessary to keep the reaction heated gently, therefore, a sufficient heating could not be given to promote the reaction. Furthermore, ethanol, ethyl acetate, etc. which are by-produced in the above-mentioned reaction process make the reflux temperature lowered and thereby there arises a problem inducing the delay of the reaction rate. Therefore, it is an important factor on the industrial preparation of the carbostyril compound (1) of the invention how the process from the compound (4) to compound (5) is carried out safely and efficiently.

DISCLOSURE OF INVENTION

Problem to be Solved by the Invention

Thus, in the process for preparing the compound (5) or the salt thereof from the compound (4) or the salt thereof which is a part of the above conventional scheme, the present inventors have extensively studied a method wherein a development of the surface caused by bubbles is depressed and which makes the preparation safely and efficiently even in a large scale, and have found that the addition of a certain specific material to the reaction system makes the bubbles depressed to prepare the useful compound (5) or the salt thereof safely and efficiently and then the desired carbostyril compound (1) or the salt thereof can be obtained by acylating the compound (5) or the salt thereof. Based upon the new findings, the present invention has been completed.

An object of the present invention is to provide an improved process for safely and efficiently preparing the carbostyril compound of the formula (1) or the salt thereof that is useful as a medicament.

It is hoped to easily and simply take a crystal of the compound (5) or the salt thereof out of the reaction mixture, which is prepared as an intermediate to prepare the desired carbostyril compound (1) or the salt thereof. In addition, it is also hoped that the compound (5) could be easily and efficiently dried in order to store it preferably as an intermediate to prepare the desired carbostyril compound (1) or the salt thereof.

Another object of the present invention is to provide a method for preventing the intense development of the surface caused by bubbles arising during the reaction and the bumping accompanied with the development in the process for preparing the compound (5) or the salt thereof from the compound (4) or the salt thereof among the sequential processes for preparing the desired carbostyril compound (1) or the salt thereof from the compound (2) or the salt thereof, by heating in the presence of a high boiling solvent suitable for the present process, and thereby to provide a process for preparing the desired carbostyril compound [the formula (1)] or the salt thereof more safely.

The other object of the present invention is also to provide a process for preparing the compound (5) or the salt thereof more efficiently through improving the above-mentioned bumping problem and additionally removing by-products at the reaction process such as ethanol, ethyl acetate, etc. according to need, in order to maintain the reflux temperature.

Furthermore, an object of the present invention is to provide a dihydrochloride dihydrate of the compound (5) as the above-mentioned desired intermediate.

Means to Solve the Problem

According to the present invention, the compound (5) or the salt thereof can be safely prepared by heating the compound (4) or the salt thereof in the presence of a high boiling solvent under acidic condition and furthermore the compound (5) or the salt thereof can be also prepared more efficiently via removing by-products in the reaction process (e.g. ethanol, ethyl acetate, etc.) according to need, in order to maintain the heat temperature, especially the reflux temperature. And then, the compound (5) or the salt thereof is acylated with 4-chlorobenzoylchloride (6) to give the desired carbostyril compound (1) or the salt thereof.

That is to say, according to the present invention, when preparing the compound (5) or the salt thereof by heating the compound (4) or the salt thereof under acidic condition, a certain specific high boiling solvent added into the reaction mixture works as an antifoaming agent to prevent undesirable bubbles, and thereby it becomes possible to fully heat the reaction mixture to promote the reaction.

In the reaction for preparing the compound (5) or the salt thereof from the compound (4) or the salt thereof, some materials having a comparatively lower boiling point (ethanol, ethyl acetate, etc.) are by-produced as the reaction proceeds. If the reaction is continued without removing them, the heat temperature, especially the reflux temperature is lowered and then the reaction cannot be sufficiently heated, so that it causes the reaction to be delayed. Accordingly, it is necessary to remove such by-produced materials having a lower boiling point out of the reaction mixture to maintain the reaction efficiency. The present invention can provide a process for preparing the compound (5) or the salt thereof more efficiently through improving the bubbling problem in order to maintain the heat temperature, especially the reflux temperature and to enhance the reaction efficiency; and also via removing the by-product of the reaction process according to need, in order maintain the temperature.

The present invention can provide a process for preparing the above-mentioned compound (5) or the salt thereof by heating the compound (4) or the salt thereof, or the desired carbostyril compound (1) or the salt thereof by acylating the compound (5) or the salt thereof, wherein the process for preparing the compound (5) or the salt thereof is carried out in water, and/or, the process for preparing the carbostyril compound (1) or the salt thereof is carried out in water or an organic solvent, or in a mixture thereof.

Furthermore, the present invention can provide a process for preparing the compound (5) or the salt thereof by heating the compound (4) or the salt thereof wherein the process is carried out in the presence of hydrochloric acid.

In addition, the present invention can provide a process for preparing the compound (5) or the salt thereof by heating the compound (4) or the salt thereof wherein the high boiling solvent used in the process is n-octanol and/or acetophenone.

The present invention can provide a novel material which is a dihydrochloride dihydrate of the compound (5) or the salt thereof prepared according to the above-mentioned process of the invention.

The high boiling solvent used in the invention should be any material which does not interrupt the process as mentioned above.

Thus, the present inventors have studied the industrial processes about each material and have found that the solvent is adapted to the above-mentioned object when the solvent is any material which can depress the development of the surface caused by the above-mentioned bubbles of carbon dioxide and can be azeotropically distilled with the solvent used for solving the acid which is used in the reaction; whose specific gravity is lower than that of the solvent including the acid; which is unmixed with the solvent including the acid and is separable from said solvent; and whose boiling point is higher than that of the solvent including the acid.

The present inventors have found that a preferable example of the acid used in the process of the invention is hydrochloric acid, and an example of the high boiling solvent suitable for the hydrochloric acid is n-octanol and/or acetophenone whose specific gravity is lower than that of hydrochloric acid and which is unmixed with hydrochloric acid and is a high boiling material, as shown especially in the following examples.

BEST MODE FOR CARRYING OUT THE INVENTION

The reaction of the invention for preparing the compound (5) or the salt thereof via acid-hydrolysis of the compound (4) or the salt thereof is carried out with the addition of a high boiling solvent in the presence of a hydrolytic catalyst. The examples of such hydrolytic catalyst include hydrohalogenic acids such as hydrochloric acid, hydrobromic acid and hydroiodic acid; mineral acids such as sulfuric acid and phosphoric acid; organic acids such as formic acid, acetic acid, trifluoroacetic acid and p-toluenesulfonic acid, and especially preferably hydrochloric acid.

The above-mentioned catalyst can be used singly or as a combination of two or more kinds of the catalysts. The water or other solvent used for solving the above-mentioned acid can be used as a solvent of the reaction and the water included in aqueous hydrochloric acid is especially preferable for the reaction solvent.

The amount of the acid used as a catalyst is not limited, however, for example, when hydrochloric acid is used as the acid catalyst, the water included in the hydrochloric acid can be used as the reaction solvent, and generally the concentration of the hydrochloric acid is 12-36%, preferably 18-22%, and the volume of the hydrochloric acid is generally 6 parts or more (preferably 8 parts or more) by volume to 1 part by weight of the compound (4) or the salt thereof.

The high boiling solvent used in the present invention exists (or is added) as a material (having an antifoaming property) which can depress the development of the surface caused by bubbles of carbon dioxide by-produced in the process for heating the above-mentioned compound (4) or the salt thereof under acidic condition; and has the following physicochemical property of the material which is unmixed with the solvent including the acid and can be azeotropically distilled with the solvent used for solving the acid which is used in the reaction, whose boiling point is higher than that of the solvent including the acid, and whose specific gravity is lower; which is not limited by the other conditions. The more detailed examples of the high boiling solvent include $C_{5-12}$ alcohols such as n-pentanol, 2-pentanol, 3-pentanol, 3-methyl-1-butanol, n-hexanol, 2-methyl-1-pentanol, 2-ethyl-1-butanol, 3-heptanol, n-octanol, n-nonanol, 3,5,5-trimethyl-1-hexanol, n-decanol, n-undecanol, and n-dodecanol; acetophenone; octylic acid; tetralin; cumene; and so on. For example, when hydrochloric acid is used as an acid catalyst and a solvent of the reaction, n-octanol and acetophenone which exhibit a physicochemical property adapted to the above-mentioned condition can be used as a more preferable high boiling solvent.

The amount of the high boiling solvent used in the reaction is not limited. And the preferable amount is variable according to the scale of bubbles, the form of the reaction vessel, etc., which is generally selected from about 0.1-3 parts by volume, preferably 0.15-1 part by volume to 1 part by weight of the compound (4) or the salt thereof.

The above-mentioned reaction is generally carried out heating at 80° C. to the reflux temperature of the reaction solvent, preferably at 100° C. to the reflux temperature of the reaction solvent and is generally completed for about 6-24 hours.

The high boiling solvent used in the process of the invention can be preferably used in the large scale preparation of the compound (5) or the salt thereof since it has a property to depress the development of the reaction surface in the process for reacting the compound (4) or the salt thereof by heating under acidic condition and can make the compound (5) or the salt thereof safely prepared and thereby the volumetric efficiency of the reaction vessel can be markedly enhanced. Regarding the reaction for preparing the compound (5) or the salt thereof form the compound (4) or the salt thereof of the invention, the compound (5) or the salt thereof of the invention can be more efficiently prepared by maintaining the heat temperature, especially the reflux temperature, removing the by-products of the reaction process according to need.

For example, the use of a Dean-Stark apparatus meets the above-mentioned two conditions simultaneously and hence the apparatus can be preferably used in industrial process.

In detail, the condensed solution consisting of the azeotropic water and the high boiling solvent is divided in two layers in the apparatus at the reflux temperature; the high boiling solvent used in the invention process is shifted in the upper layer and the by-produced low-boiling materials are shifted in the lower layer (aqueous layer; e.g. aqueous hydrochloric acid). Accordingly, by taking out only the lower layer by little and little, the low boiling materials are removed out of the reaction mixture and the required high reflux temperature is maintained to prevent the delay of the reaction, and furthermore, only the high boiling solvent in the upper layer can be cycled into the reaction vessel and used repeatedly, and the development of the surface caused by bubbles can be depressed continuously.

After the reaction is completed, the high boiling solvent is taken out without cycling to the reaction vessel, and then the high boiling solvent and the water including an acid can be recovered via the separation of such solvent. The recovered solvent can be reused directly or after an appropriate treatment.

The salt of the compound (5) of the invention obtained by the process for preparing the compound (5) or the salt thereof from the compound (4) or the salt thereof has been found to be a novel material: a dihydrochloride dihydrate of the compound (5) which had not been known.

The dihydrochloride dihydrate of the compound (5) of the invention has a better permeability compared with the other known monohydrochloride of the compound (5), and thereby the crystal thereof becomes easy to take out by means of a centrifugal machine. In addition, the dihydrochloride dihydrate of the compound (5) can be obtained in high purity because it can be obtained as a low-solvent-containing wet form due to the better permeability, thereby it is easy to remove impurities into the filtrate; and furthermore it can be efficiently prepared in large scale because it is easy to dry it; and additionally it is a novel material which is more preferable for the storage of the intermediate of the desired compound.

In addition, in an alternative process for preparing the compound (5) or the salt thereof from the compound (4) or the salt thereof, it has been found that the development of the surface caused by bubbles can be depressed to the level acceptable to the industrial preparation without adding any high boiling solvent and the reaction can be completed in a comparatively short time, when the compound (4) or the salt is heated in a mixture of hydrochloric acid and acetic acid which are mixed in a certain ratio to give the compound (5). For example, to 1 part by weight of the compound (4) or the salt thereof; hydrochloric acid can be 5-9 parts by volume, preferably 8-9 parts by volume; and acetic acid can be 2-5 parts by volume, preferably 2.5-3.5 parts by volume; and further the sum of the hydrochloric acid and the acetic acid can be about 10-12 parts by volume. And the concentration of the hydrochloric acid at this time is generally 12%-36%, preferably 18-22%. The reaction is carried out with heating generally at 100° C. or higher, preferably at reflux temperature. When the reaction is carried out through the above-mentioned specific conditions, the desired compound (5) can be obtained with a short reaction time and almost without loss of yield.

In addition, in the process for preparing the compound (5) or the salt thereof from the compound (4) or the salt thereof, an object of the present invention is to provide an efficient process for preparing the compound (5) by heating the compound (4) or the salt thereof in a mixture of hydrochloric acid and acetic acid which is suitable for the industrial preparation.

Furthermore, in the present invention, after preparing the compound (5) or the salt thereof by heating the compound (4) or the salt thereof, the compound (5) or the salt thereof is reacted with 4-chlorobenzoylchloride (6) to give the desired carbostyril compound (1). This reaction can be easily carried out by a conventional process for making an amide bind. If a suitable solvent is selected and used, the reaction solution is cooled after completing the reaction, optionally neutralized according to need, and then the precipitated crystal could be collected by filtration to easily give the divided carbostyril compound (1) or the salt thereof.

Accordingly, the process of the invention, which can get the carbostyril compound (1) prepared safely and in large scale, is a preferable industrial process for preparing the carbostyril compound (1).

The above-mentioned reaction is generally carried out using a conventional base. The base includes, for example, an alkali metal hydrogencarbonate such as lithium hydrogencarbonate, sodium hydrogencarbonate and potassium hydrogencarbonate; an alkali metal hydroxide such as lithium hydroxide, sodium hydroxide, potassium hydroxide and cesium hydroxide; an alkali metal carbonate such as lithium carbonate, sodium carbonate, potassium carbonate and cesium carbonate; an alkali metal lower alkoxide such as sodium methoxide, sodium ethoxide, potassium tert-butoxide, sodium tert-butoxide and sodium tert-pentoxide; an alkali metal hydride such as sodium hydride and potassium hydride; an alkali metal acetate such as sodium acetate and potassium acetate; a trialkylamine such as trimethylamine, triethylamine and N-ethyldiisopropylamine; pyridine; quinoline; piperidine; imidazole; picoline; dimethylaminopyridine; dimethylaniline; N-methylmorpholine; 1,5-diazabicyclo[4.3.0]non-5-ene (DBN); 1,4-diazabicyclo[2.2.2]octan-5-ene (DABCO); 1,8-diazabicyclo[5.4.0]undec-7-ene (DBU), etc. The base can be used singly or as a mixture of two or more kinds of the bases.

With regard to the ratio of the use between the compound (5) or the salt thereof and the 4-chlorobenzoylchloride (6) in the above-mentioned reaction, the use ratio of the latter is at least equimolar, preferably equimolar to 2 equivalents to that of the former. In addition, the use ratio of the base is at least equimolar to that of the 4-chlorobenzoylchloride (6).

The solvent used in the above-mentioned reaction can be a conventional solvent such as water, methanol, ethanol, propanol, butanol, acetone, acetonitrile, and ethyl acetate, which can be used singly or as a mixture of two or more kinds of the solvents.

The above-mentioned reaction can be carried out generally at about −10 to 100° C., preferably about 0 to 36° C. and then completed generally in about 5 minutes to 15 hours to give the desired carbostyril compound (1).

The material compounds (2) to (5) in Scheme 1 of the invention may be as an appropriate salt thereof or an appropriate active derivative thereof.

The carbostyril compound (1) or the salt of the invention may include stereoisomers, optical isomers, and solvates thereof such as a hydrate and ethanolate.

The carbostyril compound (1) of the invention can be easily transformed into an acid addition salt thereof by reacting with a pharmaceutically acceptable acid. The invention also includes the acid addition salt. The acid includes, for example, an inorganic acid such as hydrochloric acid, sulfuric acid, phosphoric acid, hydrobromic acid, hydroiodic acid, and nitric acid; an organic acid such as acetic acid, oxalic acid, succinic acid, maleic acid, fumaric acid, malic acid, tartaric acid, citric acid, malonic acid, methanesulfonic acid, benzoic acid, trifluoroacetic acid, benzenesulfonic acid, formic acid, and toluenesulfonic acid; and an amino acid such as arginine, aspartic acid, and glutamic acid; etc.

In addition, the carbostyril compound (1) of the invention can be easily transformed into a salt form thereof via reacting it with a pharmaceutically acceptable basic compound. The examples of the salt include a metal salt such as an alkali metal (e.g. sodium salt, potassium salt, etc.) and an alkaline earth metal salt (e.g. calcium, magnesium salt, etc.); an ammonium salt; an salt of an organic base such as trimethylamine salt, triethylamine salt, pyridine salt, picoline salt, dicyclohexylamine salt, N,N'-dibenzylethylenediamine salt, etc. The basic compound includes, for example, sodium hydroxide, potassium hydroxide, calcium hydroxide, sodium carbonate, potassium hydrogencarbonate, etc.

The carbostyril compound (1) of the invention can be micronized by means of a conventional grinding machine (mill) (e.g. Atomizer) to make the intravital absorption thereof effective. The method for preparing the micronized powder of the carbostyril compound can be micronized by a method which is well known by a skilled person. The micronization of said method can be carried out by means of a ceramic mill under appropriate conditions such as rotary rate of the mill and supply rate of the carbostyril compound (1). The micronization can also be carried out by passing the carbostyril compound (1) through an air-jetmill with an appropriate supply air-pressure during rotating the mill with appropriate supply rate and rotary rate. According to the present method, the micronized carbostyril compound (1) of the invention suitable for the formulation wherein the mean particle size is 0.5-5 μm and the 90% accumulative particle size is 10 μm or lower can be prepared.

EXAMPLE

Hereinafter, the present invention is further illustrated by examples.

Example 1

To 40 g of ethyl 2-acetamide-2-ethoxycarbonyl-3-[2(1H)-quinolinon-4-yl]propionate [the compound (4)], 400 ml of 20% hydrochloric acid and 12 ml of n-octanol were added. The mixture was reacted using a Dean-Stark apparatus to divide the solution in the apparatus. Among the divided condensed solution in the apparatus, the upper layer including n-octanol was recycled into the reaction vessel and only the lower layer was removed in about 10 to 20 ml per one hour, and the reflux was continued for 6 hours. n-Octanol was removed after 6 hours' refluxing, and then the reaction mixture was refluxed for additional 2 hours removing about 10 to 20 ml of the solvent per one hour. The reaction mixture was cooled under at 20° C. and then the precipitated crystal was collected by filtration. The crystal was washed with acetone and air-dried at about 60° C. to give 35.4 g of 2-amino-3-[2 (1H)-quinolinon-4-yl]propionate dihydrochloride dihydrate [a dihydrochloride dihydrate of the compound (5)] (yield: 97.1%).

Melting point: 295° C. (dec.)

$^1$H-NMR (DMSO-$d_6$, δ ppm) 11.81 (brs, 1H), 8.67 (brs, 3H), 7.85 (d, J=8.3 Hz, 1H), 7.54 (t, J=7.6 Hz, 1H), 7.38 (d, J=8.3 Hz, 1H), 7.24 (t, J=7.6 Hz, 1H), 6.51 (s, 1H), 4.53-4.13 (m, 1H), 3.37 (d, J=7.3 Hz, 2H).

Water content: 10.6% (calculated value: 10.6%)

HCl content: 21.0% (calculated value: 21.4%)

Elemental analysis: calc. for $C_{12}H_{18}N_2Cl_2O_5$, C: 42.24%, H: 5.31%, N: 8.21%; found C: 41.98%, H: 5.04%, N: 8.07%.

Example 2

To 80.0 g of the compound (4), 360 ml of water, 360 ml of conc. HCl, and 60 ml of acetophenone were added. The mixture was reacted using a Dean-Stark apparatus to divide the solution in the apparatus. Among the divided condensed solution in the apparatus, the upper layer including acetophenone was recycled into the reaction vessel and the lower layer was partially removed, and the reflux was continued for 10 hours at the refluxing temperature (103 to 106° C.). After that, the acetophenone was recovered via a distillation. The residue was cooled under at 20° C. and then the precipitated crystal was collected by filtration. The crystal was washed with acetone and air-dried at about 60° C. to give the desired compound (5) as a dihydrochloride dihydrate (yield: 95.6%).

Example 3

To 30 g of 2-amino-3-[2(1H)-quinolinon-4-yl]propionic acid dihydrochloride dihydrate [the dihydrochloride dihydrate of the compound (5)], 600 ml of water and 60 ml of 25% aqueous sodium hydroxide were added and the mixture was dissolved. And then, thereto a solution of 23 g of 4-chlorobenzoylchloride [the compound (6)] in 90 ml of acetone was added dropwise at ice temperature. After the addition, the reaction mixture was acidified with hydrochloric acid and then the precipitated crystal was collected by filtration. The crystal was washed with water and acetone and air-dried at about 80° C. to give 31.6 g of the carbostyril compound (1) (yield: 96.9%).

Example 4

To 20 g of the compound (4), 90 ml of water, 90 ml of conc. HCl and 60 ml of acetic acid were added and the mixture was heated to reflux for 6 hours. The solvent (125 ml) was distilled, and the residue was cooled under at 20° C. and then the precipitated crystal was collected by filtration. The crystal was washed with acetone and air-dried at about 60° C. to give the compound of the formula (5) (yield: 96.2%).

INDUSTRIAL APPLICABILITY

According to the process of the invention, the risk of the bumping can be avoided by using a high boiling solvent, and thereby the desired carbostyril compound (1) or the salt thereof can be safely prepared. Additionally the process is very useful for the large-scale preparation since the volumetric efficiency of the reaction vessel can be markedly enhanced thereby.

According to the process of the invention, the used high boiling solvent is easily recovered via the separation of the solvent removed in the middle of the reaction or in the completeness of the reaction. Additionally, from the solid-liquid-separated filtrate containing acid (hydrochloric acid), it is possible to recover a reusable acid (hydrochloric acid) via a simple distillation without throwing out the almost fraction of distillate except the initial fraction and thereby a harm to environment can be decreased.

According to the process of the invention, the compound (5) or the salt thereof can be obtained in high yield via a simple operation, the collection of the crystal by filtration after cooling, as a work-up, and accordingly the process is useful to synthesize the carbostyril compound (1) or the salt thereof in bulk.

The dihydrochloride dihydrate of the compound (5) of the invention has a better filterability compared with the other known mono-hydrochloride of the compound (5) and hence the crystal thereof is easy to take out by a centrifuge or other. In addition, the dihydrochloride dihydrate of the compound (5) can be obtained in high purity because it can be obtained as a low-solvent-containing wet form due to the better permeability, thereby it is easy to remove impurities into the filtrate. Furthermore it can be efficiently prepared in large scale because it is easy to dry it; and additionally it is a novel material more preferable for the storage of the intermediate of the desired compound.

According to the process of the invention, in an alternative process for preparing the compound (5) or the salt thereof from the compound (4) or the salt thereof, the development of the surface caused by bubbles can be also depressed to the level acceptable to the industrial preparation without adding any high boiling solvent and the reaction can be completed in a comparatively short time, when the compound (4) or the salt is heated in a mixture of hydrochloric acid and acetic acid which are mixed in a certain ratio.

The invention claimed is:

1. A process for preparing a compound of the formula (5) or a salt thereof which comprises subjecting a compound of the formula (4) or a salt thereof to the following step (a), or steps (a) and (b), (a) heating the compound of the formula (4) or the salt thereof in the presence of a high boiling solvent under acidic condition;

(b) removing a material by-produced at the step (a).

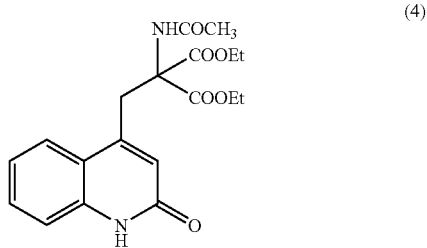

(4)

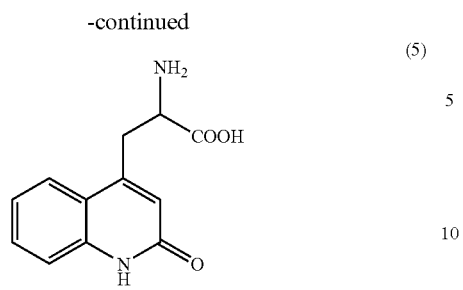

2. A process for preparing a compound of the formula (I) or a salt thereof which comprises subjecting a compound of the formula (4) or a salt thereof to the following step (a), or steps (a) and (b) to prepare a compound of the formula (5) or a salt thereof; and furthermore subjecting the compound (5) or the salt thereof to the step (c)

(a) heating the compound of the formula (4) or the salt thereof in the presence of a high boiling solvent under acidic condition;

(b) removing a material by-produced at the step (a);

(c) reacting the compound of the formula (5) or the salt thereof with 4-chlorobenzoylchloride under basic condition.

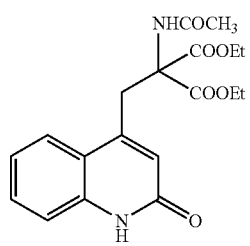

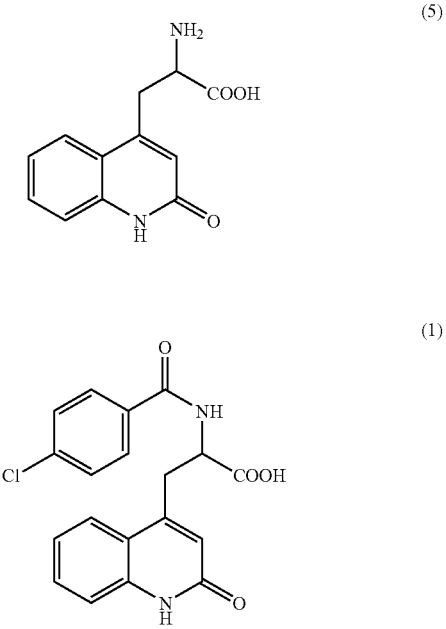

3. The process according to claim 1 or 2 wherein the step (a) is carried out in water, and/or the step (c) is carried out in water or an organic solvent, or in a mixture thereof.

4. The process according to claim 1 or 2 wherein the acidic condition of the step (a) is made with hydrochloric acid.

5. The process according to claim 1 or 2 wherein the high boiling solvent is n-octanol and/or acetophenone.

\* \* \* \* \*